United States Patent [19]
Besz et al.

[11] Patent Number: 5,099,845
[45] Date of Patent: Mar. 31, 1992

[54] MEDICAL INSTRUMENT LOCATION MEANS

[75] Inventors: William J. Besz, Pasadena; Donald P. Chorley, Torrens Park; Robert A. Walker, Hawthorndene, all of Australia

[73] Assignee: Micronix Pty Ltd., North Adelaide, Australia

[21] Appl. No.: 527,487

[22] Filed: May 23, 1990

[30] Foreign Application Priority Data

May 24, 1989 [AU] Australia ............... PJ4337

[51] Int. Cl.⁵ .................. A61B 5/05; A61B 19/00
[52] U.S. Cl. ........................... 128/653.1; 128/899
[58] Field of Search .............. 128/653 R, 657, 899, 128/658, 630; 600/13

[56] References Cited

U.S. PATENT DOCUMENTS 4,173,228  11/1979  Van Steenwyk et al. ...... 128/653 R
4,905,698   3/1990  Strohl, Jr. et al. ............... 600/13

Primary Examiner—William E. Kamm
Assistant Examiner—Kennedy J. Schaetzle
Attorney, Agent, or Firm—Townsend and Townsend

[57] ABSTRACT

An instrument location determining device which has a radiating element forming part of the instrument to be inserted into an object. The element radiates a signal and the signal is detected by at least one receiving element. A signal energy level measurement device is coupled to the receiving element and it produces an energy level value for each one of the receiving elements. The distance of the radiating elements from the receiving element is calculated from the measured energy level values received by each of the receiving elements. The measured distance is then indicated to an operator of the instrument so that he can locate the instrument within the object.

19 Claims, 5 Drawing Sheets

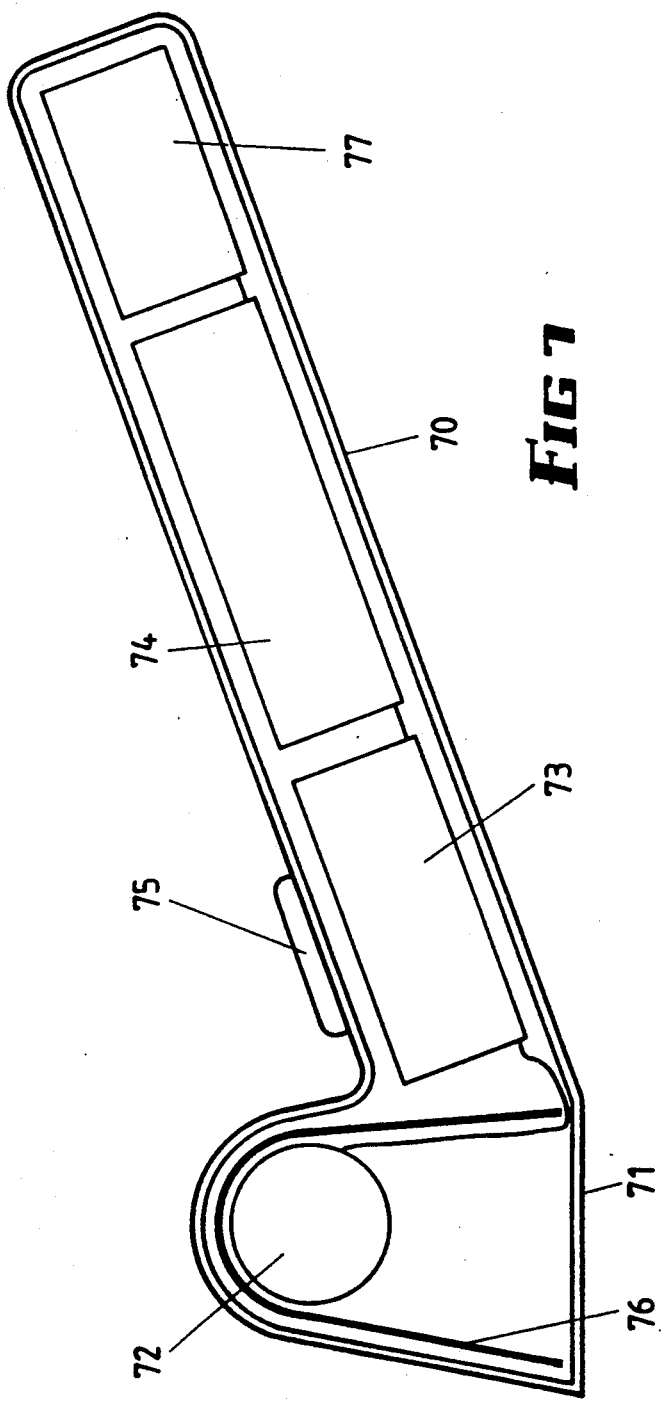
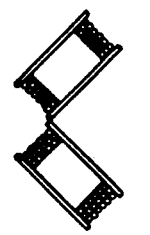
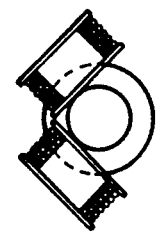
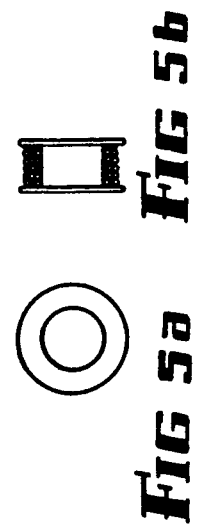

MEDICAL INSTRUMENT LOCATION MEANS

This invention relates to a location means for catheters and other like medical and other instruments while they are inserted into a body or in use in the body.

BACKGROUND OF THE INVENTION

A catheter is a medical instrument generally comprising a rigid or flexible tubular device which can be placed within a human or animal body for the purpose of administering or excising gases, liquids or medicament. The device is placed into a body via existing orifices and channels or via apertures made through the skin into veins, arteries or other like internal body spaces and channels to arrive at a site where treatment is required. The application of skill and the exercise of great responsibility by a medical practitioner is solely responsible for its proper use.

A variety of catheters are known which are usually differentiated by their design for specific purposes. For example an acorn-tipped catheter is used in ureteropyelography to occlude the ureteral orifice and prevent backflow from the ureter during and following the injection of an opaque medium; angiographic catheter is a device through which a contrast medium (i.e. X-ray opaque) is injected for visualisation of the vascular system of an organ, such catheters may have preformed ends to facilitate selective locating (as in renal or coronary vessel) from a remote entry site and thus may be further named according to the site of entry and destination, as femoral-renal, brachial-coronary, etc.; a toposcopic catheter is a very small catheter that can pass through narrow, tortuous vessels to convey chemotherapy directly to brain tumours, a Swan-Ganz catheter is a soft, flow directed catheter with a balloon at the tip for measuring pulmonary arterial pressures and is introduced into the venous system (via basilic, internal jugular, or subclavian vein) and is guided by blood flow into the superior vena cava, the right atrium and ventricle and into the pulmonary artery. Many more catheter types than described above are at the disposal of medical practitioners to use.

The ultimate worth of a catheter is determined by the accuracy of the location of the tip of the device in the body and thereafter the delivery or drainage processes acts on the organ or the part most receptive to the applied treatment. It is common practice after the catheter is placed in the body by the medical practitioner, to X-ray the patient to ensure the correct location of the catheter tip. This involves time delays and adds cost and inconvenience to the treatment process. Alternatively, this procedure of X-ray checking is not always undertaken and the skill of the practitioner must be relied upon to achieve correct location. This circumstance arises when speedy treatment is necessary and the X-ray procedure introduces unacceptable delays.

It will be apparent that a means to provide the aforementioned benefits is also capable of being used to locate other instruments that may be used in the medical or other fields.

OBJECTIVES OF THE INVENTION

Thus it is an object of this invention to provide a location means which is capable of identifying the location of an instrument or any other chosen part of the device while the instrument is inserted in a body or other object.

A further object of this invention is to provide a location means applicable to the task of locating the tip of a catheter or other like medical instrument or device which is fitted with a location means which is introduced into the body of humans or animals.

BRIEF DESCRIPTION OF THE INVENTION

In its broadest form the invention comprises an instrument location determining apparatus comprising a radiating element incorporated within an instrument to be inserted into an object wherein said element radiates signal energy, a signal energy detector means comprising at least one receiving element oriented to receive the radiated signal energy, a signal energy level measurement means coupled to the receiving element so as to produce an energy level value for each one of said receiving elements coupled to the measurement means, a calculation means which calculates using the measured energy level values received in each of the said receiving elements the distance of the radiating element from the receiving elements, an indication means coupled to said calculation which provides to an operator of the apparatus an indication of the distance calculated so that the instrument may be located within the object.

A preferred embodiment of the invention will now be described, but it will be understood by those skilled in the art that the invention need not be limited to any one or combination of the features disclosed.

BRIEF DESCRIPTION OF THE DRAWINGS

FIGS. 5a and 5b show an embodiment of the coil receiving element;

FIGS. 6a and 6b show embodiments of two configurations of coil receiving elements;

FIG. 7 shows a cross-sectional view of an embodiment of a hand-held distance measuring device;

DETAILED DESCRIPTION OF THE DRAWINGS

Figure 1:
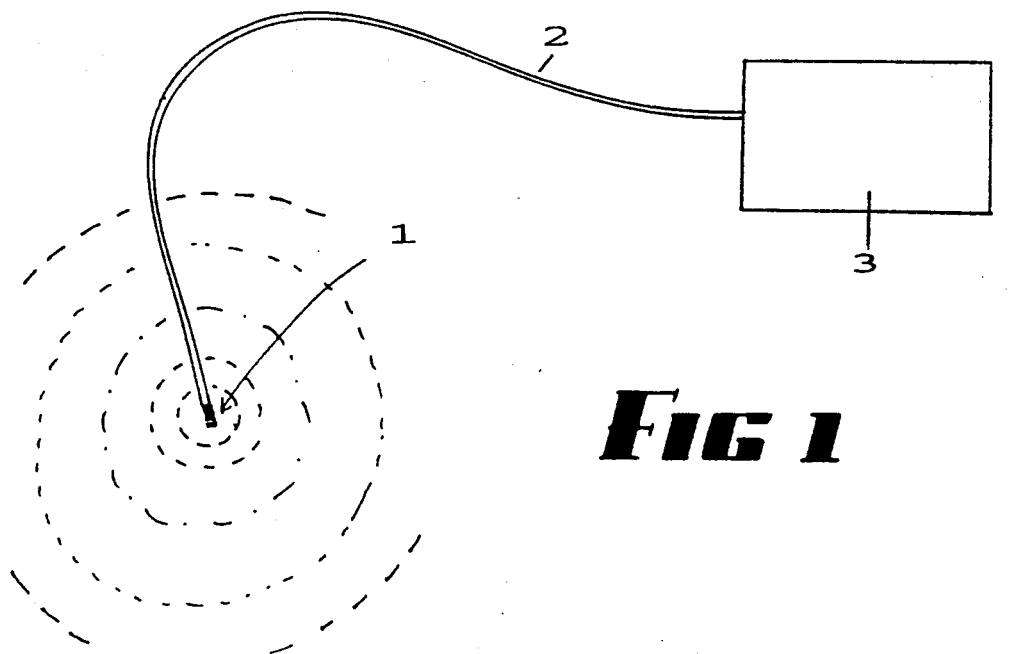
FIG. 1 shows a catheter comprising a tuned coil and integral electromagnetic source.

The embodiment of a radiating element shown in FIG. 1 comprises a fine gauge of wire 1 wrapped in an helical pattern about the tip of a catheter 2. This winding could comprise one or more windings and ideally is of the finest gauge of conductive wire such that a small number of turns is used to provide resultant complex impedance capable of interacting with a capacitive element and combine with the remainder of a circuit 3 to provide a coil tuned to radiate most efficiently at a desired frequency. In this preferred embodiment a frequency of 40 kHz was chosen, however it would be apparent to those skilled in the art that any number of frequencies which exhibited least attenuation through the body of interest and to which a coil of specified turns, gauge of wire and diameter of coil could be tuned would be possible. An alternative device to this type of radiating device could be a chip device comprising inductance and capacitive elements capable of radiating an electromagnetic field either in a particular direction or omni-directionally. Alternatively the radiating element may comprise a straight wire configuration having added capacitive elements in series to act as radiator of electromagnetic energy.

In this embodiment the oscillator circuit comprises a crystal driven 40 kHz square wave oscillator operated continuously and at a predetermined voltage amplitude. However, it will be apparent that the oscillator may comprise a variety of circuit means operating at various other frequencies or combinations thereof and that the resultant radiated energy may be made adjustable so that the radiating element of the apparatus may be matched to the receiving elements to calibrate the distance measurement made.

The choice of a frequency of operation and required signal strength is dependent upon the nominal impedance of the electromagnetic radiation through body tissue and bone and the required signal energy required for operation of the receiving elements over a useable range, therefore, greater oscillator signal strength or judicious choice of frequency is required to achieve best results from the invention in the environment of its application.

A catheter is a sterilised instrument and it is necessary that the coil is encapsulated as part of the catheter preferably in a substance inert to the body environment. However, it is possible for further embodiments of the coil configuration to be encapsulated within the catheter itself or at points along its length.

Additionally, the oscillator means may be incorporated into the tip of the catheter and the use of the radiating device in these circumstances may occur only once.

In an application of this type the oscillator means, may, for reasons of the need to reduce power consumption, be non-continuous i.e. pulsed operation in a coded or non-coded manner.

This variety of oscillator methods could then support a plurality of radiating devices in the same body and allow individual location of each of the different catheter devices. Of course after correct location is achieved an oscillator attached to the radiating element can be stopped if it is external to the body or alternatively again the oscillator device if completely internal could have a receiver means which is responsive to external communication means to command it to stop, start and perform other functions as required.

It will also be apparent that additional means of providing a radiating element can be used such as an ultrasonic transducer which can exhibit similar characteristics to that of the electromagnetic radiating element.

Figure 2:
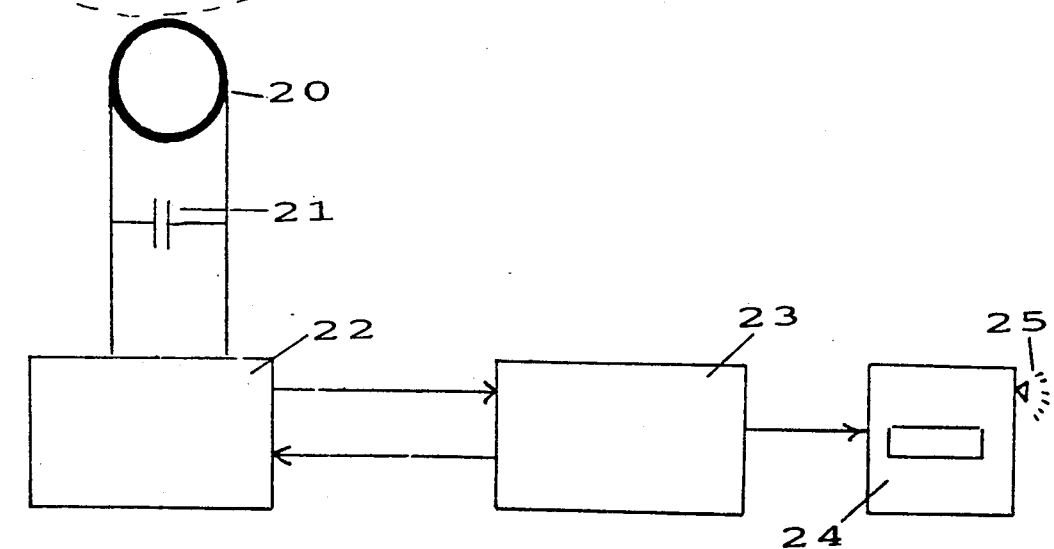
FIG. 2 shows a single coil receiving device and associated control and processing means.

FIG. 2 shows a single coil radiation receiving element comprising a wire wound coil 20 and shown schematically a capacitive element 21 to depict the tuned nature of the coil. In this embodiment the tuned frequency of the receiving coil is 40 kHz and its output is fed to an amplifier means 22 which is further processed by circuit means and microprocessor 23 to provide data relating to the distance the radiating coil is from the receiving coil or coils. This information is then indicated by visual 24 and audible 25 means to the medical practitioner who is thus able to trace and manipulate the catheter during its travel internally through the body.

Figure 4:
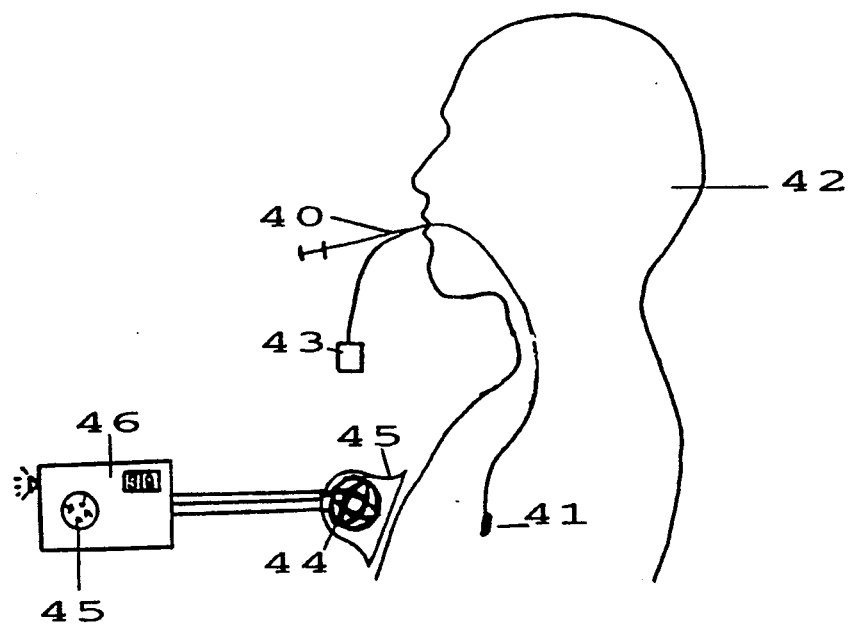
FIG. 4 shows a catheter according to the invention in use.

The display could have many forms, in this embodiment the operation of a series of lights as shown in FIG. 4 at 45 provides a human readable output of the direction and distance of the radiating coil which is located on the tip of the catheter in relation to the receiving coils outside the body. Additionally an audible indication means 25 comprising the production of a high rate of repetition of tone burst to indicate the close proximity of the receiving coils to the catheter tip. The use of one coil provides a location indication only in one plane.

Figure 3:
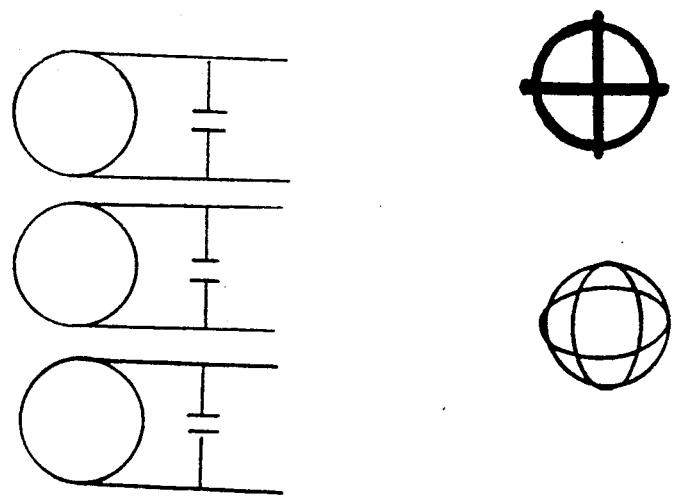
FIG. 3 shows a three axis coil receiving device.

FIG. 3 shows a three coil receiving arrangement. The coils are oriented with their longitudinal axes orthogonal to one another and after reception and amplification three separate signals representative of the energy received in three different planes can be used by the central processing device to calculate and indicate the distance of the radiating element from the receiving element. The display of this information can take many forms, however, in this embodiment as shown in FIG. 4 at 45 the graphic display of a computer device provides feedback to the medical practitioner administering the catheter to the patient of its x and y positions relative to the hand held receiving coils. The distance measurement provides the z axis value. If a coil on the tip of a catheter is used, the orientation of the coil may also be determined and displayed if this is critical to the treatment being provided. Additional programming of the processor device is required to provide this feature.

FIG. 4 is an illustration of a catheter 40 fitted with a radiating coil 41 located in the chest cavity of a person 42. Although not shown explicitly the radiating element is powered by an energy source/oscillator circuit 43 which is located external to the body, however, a power source/oscillator circuit could be integrated with the radiating coil and thus be capable full insertion into the body at the end or any other position of the catheter.

The receiving coil array 44 is shown as being incorporated into a hand-held unit 46. The location of the radiating element 41 is determined by moving the unit 46 about the surface of the body until a suitable audio signal is emitted by the unit. When the catheter tip is located the depth of the radiating element from the receiving coil is calculated and displayed and indicated to provide the depth of the catheter tip from the surface of the body thereby assisting the physician in determining the exact location of the radiating element in the body. The physician's knowledge of the anatomy and arrangement of the organs of the body is combined with the information supplied by the device to enable the physician to be more confident of its location.

An example of such a procedure's practical application is the task of inserting a catheter/tube into the trachea so that anaesthetic and/or air may be administered directly to the lungs without accidently inserting the catheter into the oesophagus.

The path of such a catheter diverges into the trachea from the larynx and beyond the branch point the depth of the tube may be tracked to increase the confidence of the physician that it has entered the correct part of the body.

Where paths diverge which have the same depth, the location of the catheter tip can be determined by its position on the surface of the body.

FIG. 5 shows an embodiment of a receiving coil which has been wound on a 8.5 mm diameter by 7 mm wide former consisting of 400 turns of 0.12 mm o.d. wire.

FIG. 6a shows the top view of an embodiment of the configuration of a two coil detector, while FIG. 6b shows a top view of a three coil detector. Note that the longitudinal axis of each of the coils are at 90° to each other.

FIG. 7 shows a cross-sectional view of an embodiment of a hand held unit comprising a body 70 having a substantially smooth flat surface 71 above which and internal to the body the detection coils 72 of FIG. 6a or 6b are located. These coils are connected to amplification circuit 73 located in the body of the unit which in turn is connected to the calculation circuit 74 and display circuit 75 of the hand held unit. A concave shield 76 made of material which is shaped and has properties which restrict the reception by the coils of radiation to only that which enters the hand held unit body from the surface 71 is located above and about the surface 71. In this embodiment the shield comprises a cup like structure made of Mumetal or other like high-permeability, low saturation magnetic alloy. A battery 77 supplies a direct current power source to the circuits 73, 74 and display 75. The battery may be of the rechargeable type.

Figure 8:
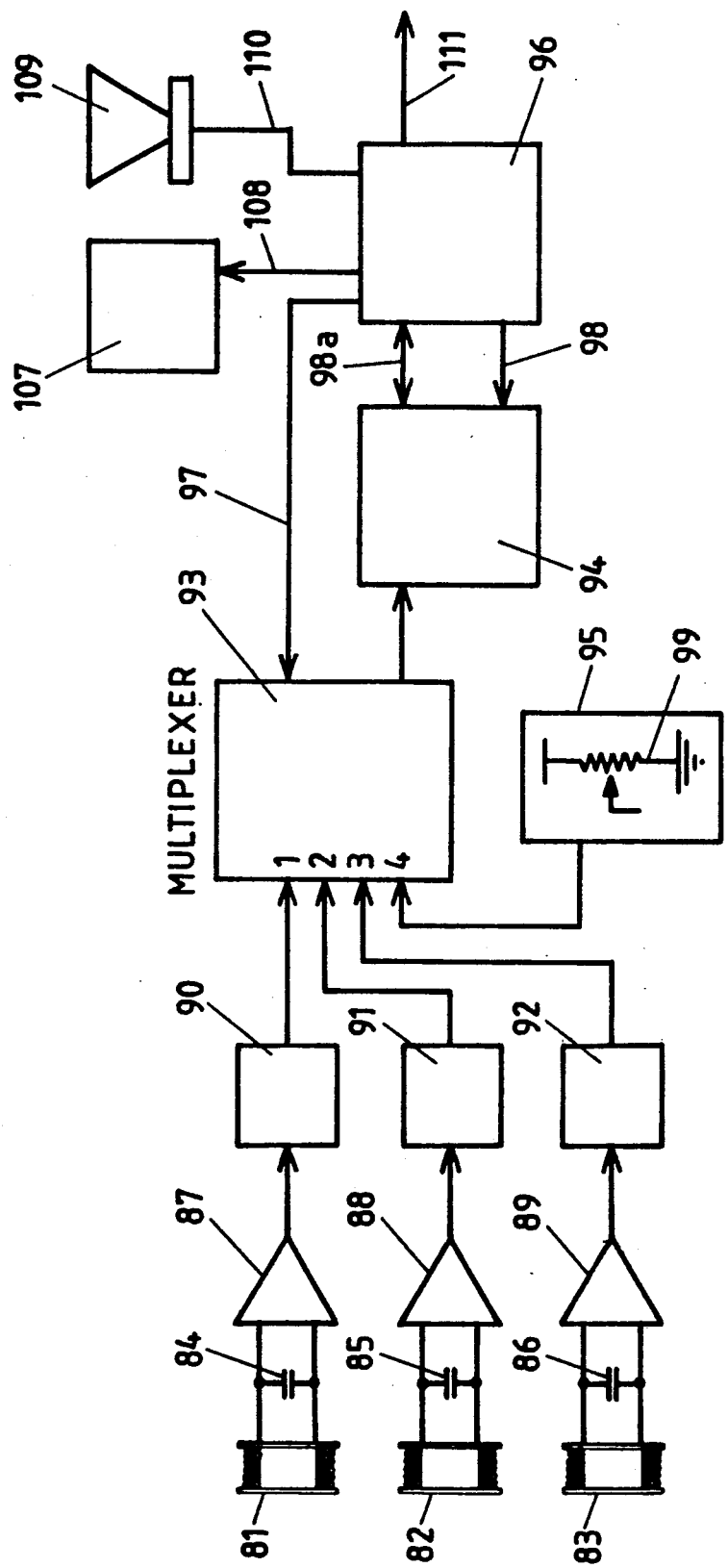
FIG. 8 shows a block diagram of the circuit of the hand held distance measuring device.

FIG. 8 shows a block diagram of the circuit of the hand held device. Two or three coils 81, 82, 83 may be used, each coil being tuned for optimum conversion of the impinging 40 kHz signal emanating from the radiating element. The coils 81, 82 and 83 become resonant at this frequency when combined with the capacitive elements 84, 85 and 86 respectively. A signal proportional to the strength of the received signal is amplified by respective amplifiers 87, 88 and 89 (NE5534) which are in this embodiment set to provide a gain of approximately 200. Optionally, filter circuits (not shown) may be used to narrow the band of the received and amplified signals from the coils and reduce the influence of extraneous signals and amplifier noise. The amplified alternating current signals are converted into a direct current by converters 90, 91 and 92 (LF356) respectively after which they are directed to a multiplexing device 93 (4052) which in turn applies the respective values of the detected signals at the coils to a 12 bit analogue to digital converter 94 (7109). A direct current reference voltage is provided by reference unit 95 against which the detected coil signals may be compared and calibrated so that the measurements made are always relative to a constant. However the main use of this variable direct current voltage reference is to provide an adjustment means via a variable resistance 99 to allow the calculated distance to be adjusted to reflect the actual distance between the coil and the radiating element.

A micro processor device 96 (87C51) provides control signals along connection wire 97 to the multiplexing device 93 such that each receiving coil signal and the reference voltage in the form of a representative direct current voltage is applied in turn to the analogue to digital converter device 94.

The microprocessor device 96 also provides control signals along connecion wire 98 to the analogue to digital converter 94 to enable the flow of digital data from the converter 94 to the microprocessor via connection 98a. This data is a digital representation of the direct current voltage signals received at the three coils 81, 82 and 83 as well as the voltage of the d.c. reference 95. These values are used by the microprocessor to calculate the distance of the radiating element from the receiving coil array. After the distance has been calculated the microprocessor can offset the value of distance displayed to reflect the difference between the receiving coil distance to the radiating coil and the receiving coil distance to the hand held unit surface 71. It is the later distance which is most useful to the practitioner.

Figure 9:
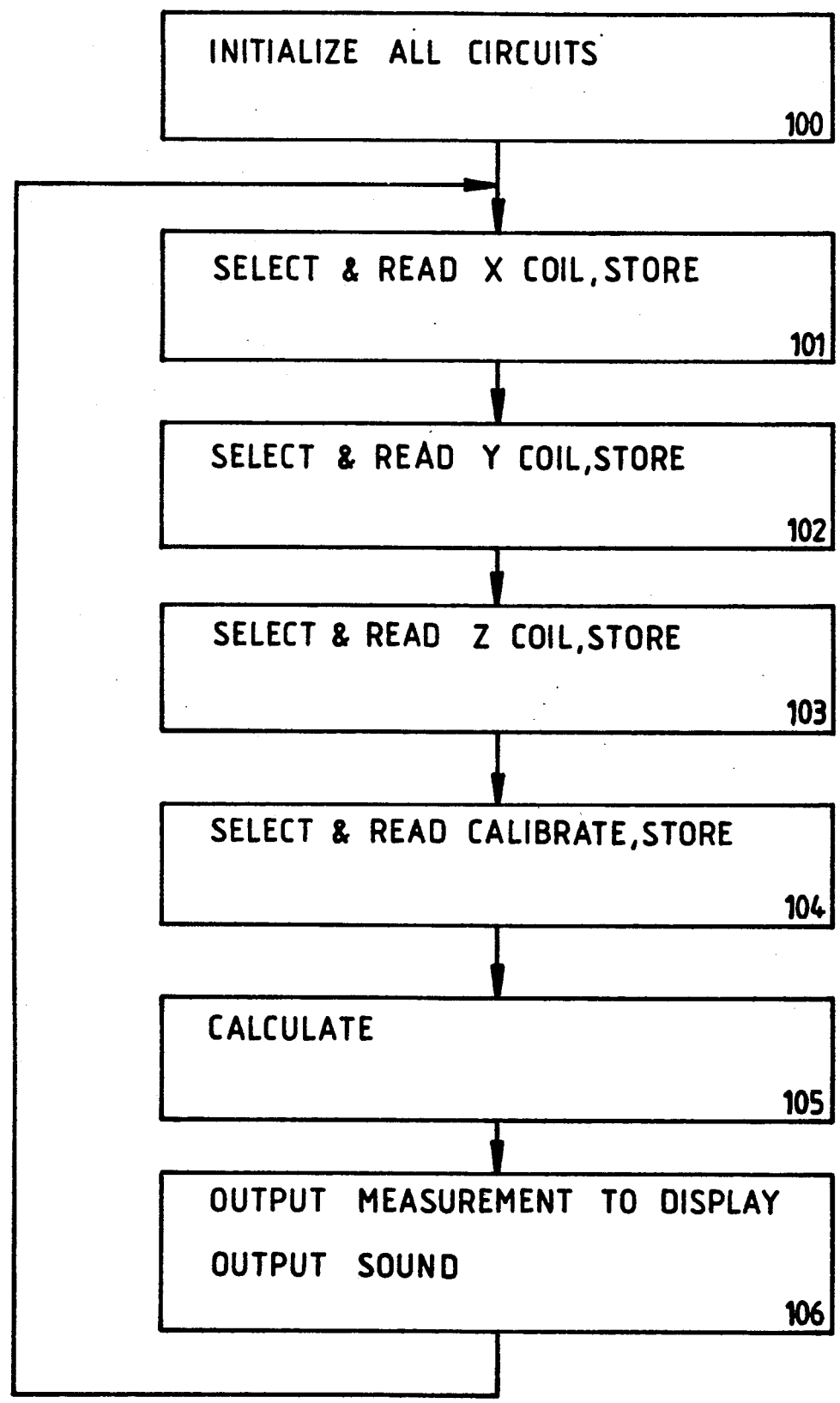
FIG. 9 shows a flow diagram of the measurement program of the microprocessor.

FIG. 9 shows a flow diagram of the measurement program of the microprocessor and its control of various selections of data input to collect the data required to make the calculation. Step 100 is an initialisation phase where all registers associated with storing values for the calculation are set to zero and all select lines are disabled. Step 101 follows and indicates that select line 97 is set to switch the multiplexer 93 to pass the direct current signal value of coil 82 through to the analogue to digital converter 94. After a preset delay control line 98 is selected to enable the transfer of the representative digital value of the voltage signal in the coil 81 into a memory storage register of the microprocessor 96 via connection 98a and is represented by a value x.

Step 102 repeats the same process as step 101 except that the voltage signal of coil 82 is transferred into a memory storage register of microprocessor 96 and is represented by a value y.

Likewise Step 103 is the same as steps 101 and 102 as per coil 83 if it is used and its voltage signal is transferred into a memory storage register of microprocessor 96 and is represented by a value z.

Step 104 is not unlike steps 101, 102 and 103 except that the voltage of the direct current reference is transferred into a memory storage register of microprocessor 96 and is represented by a value k.

Step 105 is a calculation of the distance, d, from the common axis point of the coils to the radiating element which conforms to the formula:

$$d = k \cdot \sqrt[3]{\frac{1}{\sqrt{(e_1)^2 + (e_2)^2 + \ldots (e_p)^2}}}$$

Wherein $e_1, e_2, \ldots e_p$ represent energy levels received by each of the receiving coils. In the instant case, $$d = k \cdot \sqrt[3]{\frac{1}{\sqrt{x^2 + y^2 + z^2}}}$$

The values k, x, y and z are obtained from the various registers and the calculation performed to provide a value d.

The value d can be represented to 3 significant figures on the liquid crystal display 107 via connection 108 in the form for example as 10.5 which represents 10.5 cm. For ease of display and readability the mircroprocessor 96 only increments the distance display in 0.5 mm steps for example 10.0–10.5–11.0 when the values of d is greater than 10.0 and provides 0.1 increments for values of d less than 10.0 while also providing time delays for each transition so that the value does not change in a spurious or unnecessarily hard to read fashion.

As described previously, the value of k represents the direct current voltage reference value and changes by varying the value of resistor 99. This direct control of the displayed distance value is preferable so as to reflect the actual measured distance of the coils from a radiating element. It will also be apparent that the radiating element energy could be likewise adjusted if the reference voltage were fixed however it has been found that adjustment of the reference voltage is more practical.

Since the physician controlling the administration of the catheter or like device to the body of the patient is not always able to observe the distance measurement displayed an audible indication of depth is also provided. An output of the microprocessor is controlled within step 106 of the flow diagram to drive an audio transducer 109 for example a piezoelectric device via connection 110.

The exact form of the audio signal is a matter of convenience however it has been found that a constant volume pulse of tone (e.g. 1 kHz for 0.3 seconds) which increases its repetition rate the smaller the value of d, is most useful and acceptable as a means of location indication after which the distance value can be ascertained from the liquid crystal display.

The microprocessor 96 is also able to output all the values x, y, z, k and d to other computer devices via its RS232C output port 111. This data can then be recorded, logged or used to provide more visual means of display when combined with other data.

It will be apparent to those skilled in the art that the radiating element may comprise an element other than a coil such as for example an ultrasonic transmitter which worked in conjunction with an ultrasonic receiving element or elements. It is also apparent that two electromagnetic signal receiving coils arranged at right angles to each other as shown in FIG. 6a would also suffice to accomplish the objects of the invention.

It will also be apparent that the elements of the invention are equally applicable to the location of a great many medical and other instruments which are used out of normal view of their operators and for which a non-intrusive distance and location indication means would provide additional assurance to the operator.

For example, tubes and shapes placed into the body for all manner of purposes could be fitted with self-contained or remotely powered radiating elements which may then be located.

The claims defining the invention are claimed as follows:

1. An instrument location determining apparatus comprising an instrument and a radiating element incorporated within the instrument to be inserted into an object wherein said element radiates signal energy, a signal energy detector means comprising
    at least one receiving element oriented to receive the radiated signal energy,
    a signal energy level measurement means coupled to the receiving element so as to produce an energy level value for each one of said receiving elements coupled to the measurement means,
    a calculation means which calculates using the measured energy level values received in each of the said receiving elements the distance of the radiating element from the receiving elements,
    an indication means coupled to said calculation which provides to an operator of the apparatus an indication of the distance calculated so that the instrument may be located within the object.

2. An instrument location determining apparatus according to claim 1 wherein said instrument is a catheter.

3. An instrument location determining apparatus according to claim 2 wherein the radiating element is a coil located at the tip of a catheter inserted into a body.

4. An instrument location determining apparatus according to claim 1 wherein energy levels received be each one of said receiving elements is represented by values $e_1, e_2, \ldots, e_p$ whereby the calculation means uses the energy level values for each receiving element respectively according to the formula $$d = \sqrt[3]{\frac{1}{\sqrt{(e_1)^2 + (e_2)^2 + \ldots + (e_p)^2}}}$$

to determine the distance d of the radiating element from the receiving elements.

5. An instrument location determined apparatus according to claim 4 wherein the calulation means calculates the distance of the receiving elements from the radiating element.

6. An instrument location determining apparatus according to claim 5 wherein the signal energy level measurement means comprises an adjustable direct current voltage source having a signal value k and an output which is connected to an input of the signal selection means whereby the control means controls the signal selection means to switch the direct current voltage to its output wherein the calculation means calculates according to the formula $$d = k \cdot \sqrt[3]{\frac{1}{\sqrt{(e_1)^2 + (e_2)^2 + \ldots + (e_p)^2}}}$$

the distance d of the receiving coils from the radiating coil and wherein the value of k can be adjusted to adjust the distance value measured and indicated to an absolute distance measurement.

7. An instrument location determining apparatus according to claim 1 wherein the radiating element is a coil energised to radiate an electromagnetic signal, and
    said receiving element comprises a coil incorporated within a tuned circuit, tuned to receive said radiated electromagnetic signal.

8. An instrument location determining apparatus according to claim 7 wherein each one of said receiving elements is orientated differently to each other so as to receive different energy levels of the radiated electromagnetic signal from the radiating element.

9. An instrument location determining apparatus according to claim 8 wherein the coil radiates a signal of preset energy and frequency.

10. An instrument location determining apparatus according to claim 9 wherein the preset frequency is 40 kHz.

11. An instrument location determining apparatus according to claim 9 wherein the signal energy level measurement means comprises an amplifier means for amplifying the received signal energy of the tuned circuit whereby the signal comprises a varying alternating voltage signal.

12. An instrument location determining apparatus according to claim 11 wherein the signal energy level measurement means further comprises a signal conversion means for each of the receiving elements for converting the varying alternating voltage to a varying direct current voltage.

13. An instrument location determining apparatus according to claim 12 wherein the signal energy level measurement means further comprises signal selection means having a plurality of inputs from the signal conversion means of each receiving element and an output for selecting one of its inputs to be directed to its output.

14. An instrument location determining apparatus according to claim 13 wherein the signal energy level measurement means further comprises an analogue to digital conversion means having an input coupled to the output of the signal selection means for converting the varying direct current signal to a digital value representative of the signal energy level selected by the selection means corresponding to a receiving element.

15. An instrument location determining apparatus according to claim 14 wherein there is a connection means between the signal energy level measurement means and the calculation means, comprising
  memory storage means, the said calculation means comprises control means to control the signal selection means to direct the signal energy level of a receiving element to the output of the signal selection means and to control the recording of the digital value of the signal energy level in the memory storage means.

16. An instrument location determining apparatus according to claim 1 wherein the indication means comprises a human readable display of the distance calculated.

17. An instrument location determining apparatus according to claim 6 wherein the display comprises a liquid crystal numeric display device.

18. An instrument location determining apparatus according to claim 1 wherein the indicator means comprises a human audible indication of the distance calculated.

19. An instrument location determining apparatus according to claim 18 wherein the audible indication comprises an audible tone gated on and off at a rate which increases for small distance values and decreases for large distance values about a median distance value of the distance measured at range of the apparatus.

* * * * *